US010206670B2

(12) United States Patent
Thornes

(10) Patent No.: US 10,206,670 B2
(45) Date of Patent: *Feb. 19, 2019

(54) APPARATUSES AND METHODS FOR FIXATION OF ANKLE SYNDESMOSIS OR ACROMIOCLAVICULAR JOINT DISLOCATIONS OF THE SHOULDER

(71) Applicant: ARTHREX, INC., Naples, FL (US)

(72) Inventor: Brian Thornes, Sutton (IE)

(73) Assignee: ARTHREX, INC., Naples, FL (US)

(*) Notice: Subject to any disclaimer, the term of this patent is extended or adjusted under 35 U.S.C. 154(b) by 370 days.

This patent is subject to a terminal disclaimer.

(21) Appl. No.: 14/933,269

(22) Filed: Nov. 5, 2015

(65) Prior Publication Data

US 2016/0051250 A1 Feb. 25, 2016

Related U.S. Application Data

(60) Continuation of application No. 13/970,269, filed on Aug. 19, 2013, now abandoned, which is a division of
(Continued)

(30) Foreign Application Priority Data

Jun. 20, 2002 (IE) .................................. S2002/0504

(51) Int. Cl.
*A61B 17/04* (2006.01)
*A61B 17/68* (2006.01)
(Continued)

(52) U.S. Cl.
CPC ........ *A61B 17/0401* (2013.01); *A61B 17/068* (2013.01); *A61B 17/68* (2013.01);
(Continued)

(58) Field of Classification Search
CPC ........ A61B 17/0401; A61B 2017/0404; A61B 2017/044
See application file for complete search history.

(56) References Cited

U.S. PATENT DOCUMENTS 2,765,787 A 10/1956 Pellet
3,176,316 A 4/1965 Bodell
(Continued)

FOREIGN PATENT DOCUMENTS

DE 29910202 U1 9/1999
DE 20101791 U1 6/2001
(Continued)

OTHER PUBLICATIONS

E.P. Su, et al., "Using Suture Anchors for Coracoclavicular Fixation in Treatment of Complete Acromioclavicular Separation," The American Journal of Orthopedics, May 2004, pp. 256-257.

*Primary Examiner* — Kathleen Holwerda
*Assistant Examiner* — Christina Lauer
(74) *Attorney, Agent, or Firm* — Carlson, Gaskey & Olds

(57) ABSTRACT

A method of ankle syndesmosis repair according to an exemplary aspect of the present disclosure includes, among other things, drilling a hole through a fibula and a tibia of an ankle joint, pulling a first button device through the hole using a pull-through suture until the first button device exits on a medial side of the tibia, flipping the first button device so it rests against a medial cortex of the tibia, and positioning a second button device at a lateral side of the fibula.

10 Claims, 11 Drawing Sheets

Related U.S. Application Data application No. 11/482,038, filed on Jul. 7, 2006, now Pat. No. 8,512,376, which is a continuation-in-part of application No. 10/233,122, filed on Aug. 30, 2002, now Pat. No. 7,235,091.

(60) Provisional application No. 60/697,125, filed on Jul. 7, 2005.

(51) Int. Cl.
    *A61B 17/068*      (2006.01)
    *A61B 17/86*      (2006.01)
    *A61B 17/56*      (2006.01)

(52) U.S. Cl.
    CPC ........ *A61B 17/86* (2013.01); *A61B 2017/044* (2013.01); *A61B 2017/0404* (2013.01); *A61B 2017/564* (2013.01)

(56) References Cited

U.S. PATENT DOCUMENTS

| | | |
|---|---|---|
| 4,187,558 A | 2/1980 | Dahlen et al. |
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 4,988,351 A | 1/1991 | Paulos et al. |
| 5,024,669 A | 6/1991 | Peterson et al. |
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,219,359 A | 6/1993 | McQuilkin et al. |
| 5,263,984 A | 11/1993 | Li et al. |
| 5,266,075 A | 11/1993 | Clark et al. |
| 5,306,290 A | 4/1994 | Martins et al. |
| 5,306,301 A | 4/1994 | Graf et al. |
| 5,320,626 A | 6/1994 | Schmieding |
| 5,397,357 A | 3/1995 | Schmieding et al. |
| 5,409,490 A | 4/1995 | Ethridge et al. |
| 5,562,669 A | 10/1996 | McGuire |
| 5,575,819 A | 11/1996 | Amis et al. |
| 5,628,756 A | 5/1997 | Barker et al. |
| 5,643,266 A | 7/1997 | Li et al. |
| 5,645,588 A | 7/1997 | Graf et al. |
| 5,830,234 A * | 11/1998 | Wojciechowicz ........................ A61B 17/06166 606/224 |
| 5,921,986 A | 7/1999 | Bonutti et al. |
| 5,931,869 A | 8/1999 | Boucher et al. |
| 5,961,520 A | 10/1999 | Beck, Jr. et al. |
| 5,964,764 A | 10/1999 | West et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,117,160 A | 9/2000 | Bonutti |
| 6,159,234 A | 12/2000 | Bonutti et al. |
| 6,193,754 B1 | 2/2001 | Seedhom |
| 6,203,572 B1 | 3/2001 | Johnson et al. |
| 6,238,395 B1 * | 5/2001 | Bonutti .............. A61B 17/0401 606/215 |
| 6,283,996 B1 | 9/2001 | Chervitz et al. |
| 6,296,659 B1 | 10/2001 | Foerster |
| 6,325,804 B1 | 12/2001 | Wenstrom, Jr. et al. |
| 6,517,578 B2 | 2/2003 | Hein |
| 6,533,802 B2 | 3/2003 | Bojarski et al. |
| 6,635,073 B2 | 10/2003 | Bonutti |
| 6,641,596 B1 | 11/2003 | Lizardi et al. |
| 6,716,234 B2 | 4/2004 | Grafton et al. |
| 7,097,654 B1 | 8/2006 | Freedland |
| 7,235,091 B2 | 6/2007 | Thornes |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,057 B2 | 1/2011 | Cook et al. |
| 7,875,058 B2 | 1/2011 | Holmes, Jr. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 8,388,655 B2 | 3/2013 | Fallin et al. |
| 8,512,376 B2 | 8/2013 | Thornes |
| 8,821,551 B2 | 9/2014 | Zeetser et al. |
| 9,259,217 B2 | 2/2016 | Fritzinger et al. |
| 2001/0041938 A1 | 11/2001 | Hein |
| 2002/0019634 A1 | 2/2002 | Bonutti |
| 2002/0161439 A1 | 10/2002 | Strobel et al. |
| 2002/0198527 A1 * | 12/2002 | Muckter ............ A61B 17/1671 606/254 |
| 2003/0114929 A1 | 6/2003 | Knudsen et al. |
| 2003/0130694 A1 | 7/2003 | Bojarski et al. |
| 2003/0236555 A1 | 12/2003 | Thornes |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0116963 A1 | 6/2004 | Lattouf |
| 2004/0236373 A1 | 11/2004 | Anspach, III |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0095130 A1 | 5/2006 | Caborn et al. |
| 2006/0142769 A1 | 6/2006 | Collette |
| 2006/0190041 A1 | 8/2006 | Fallin et al. |
| 2006/0264944 A1 | 11/2006 | Cole |
| 2006/0265064 A1 | 11/2006 | Re et al. |
| 2007/0021839 A1 | 1/2007 | Lowe |
| 2007/0083236 A1 | 4/2007 | Sikora et al. |
| 2007/0118217 A1 | 5/2007 | Brulez |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0046009 A1 | 2/2008 | Albertorio et al. |
| 2008/0082128 A1 | 4/2008 | Stone |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0195148 A1 | 8/2008 | Cook et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |

(56) References Cited

U.S. PATENT DOCUMENTS

| | | |
|---|---|---|
| 2009/0018654 A1 | 1/2009 | Schmieding et al. |
| 2009/0030516 A1 | 1/2009 | Imbert |
| 2009/0036893 A1 | 2/2009 | Kartalian et al. |
| 2009/0054982 A1 | 2/2009 | Cimino |
| 2009/0062854 A1 | 3/2009 | Kaiser et al. |
| 2009/0082805 A1 | 3/2009 | Kaiser et al. |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bárdos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0224729 A1 | 9/2011 | Baker et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0282350 A1 | 11/2011 | Kowarsch et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |
| 2013/0331886 A1 | 12/2013 | Thornes |
| 2017/0209196 A1 | 7/2017 | Zajac et al. |

FOREIGN PATENT DOCUMENTS

| | | |
|---|---|---|
| EP | 0440991 A1 | 8/1991 |
| EP | 1108401 A1 | 6/2001 |
| EP | 1707127 A1 | 10/2006 |
| EP | 2238944 A2 | 10/2010 |
| WO | 2007/002561 A1 | 1/2007 |
| WO | 2008/091690 A1 | 7/2008 |

\* cited by examiner

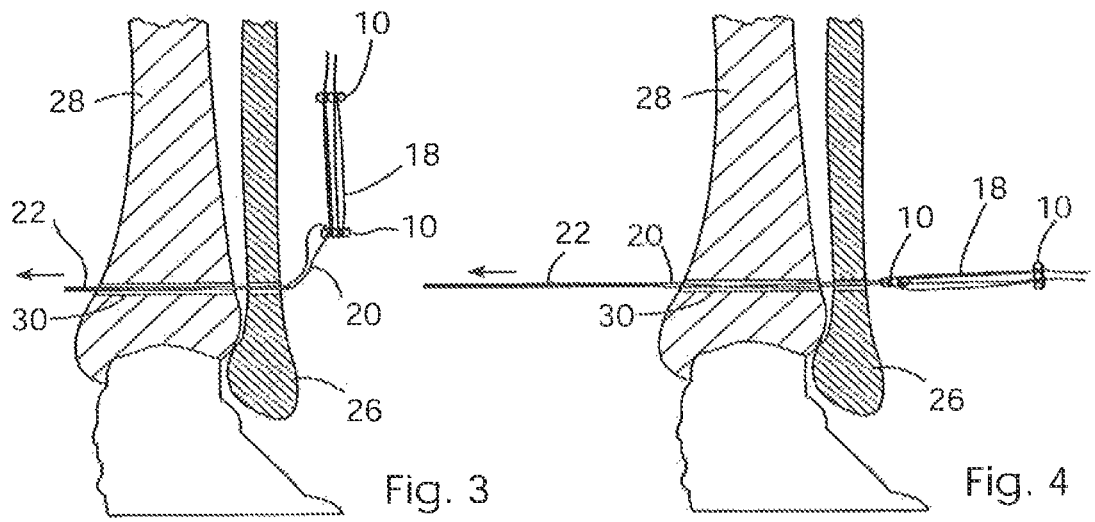
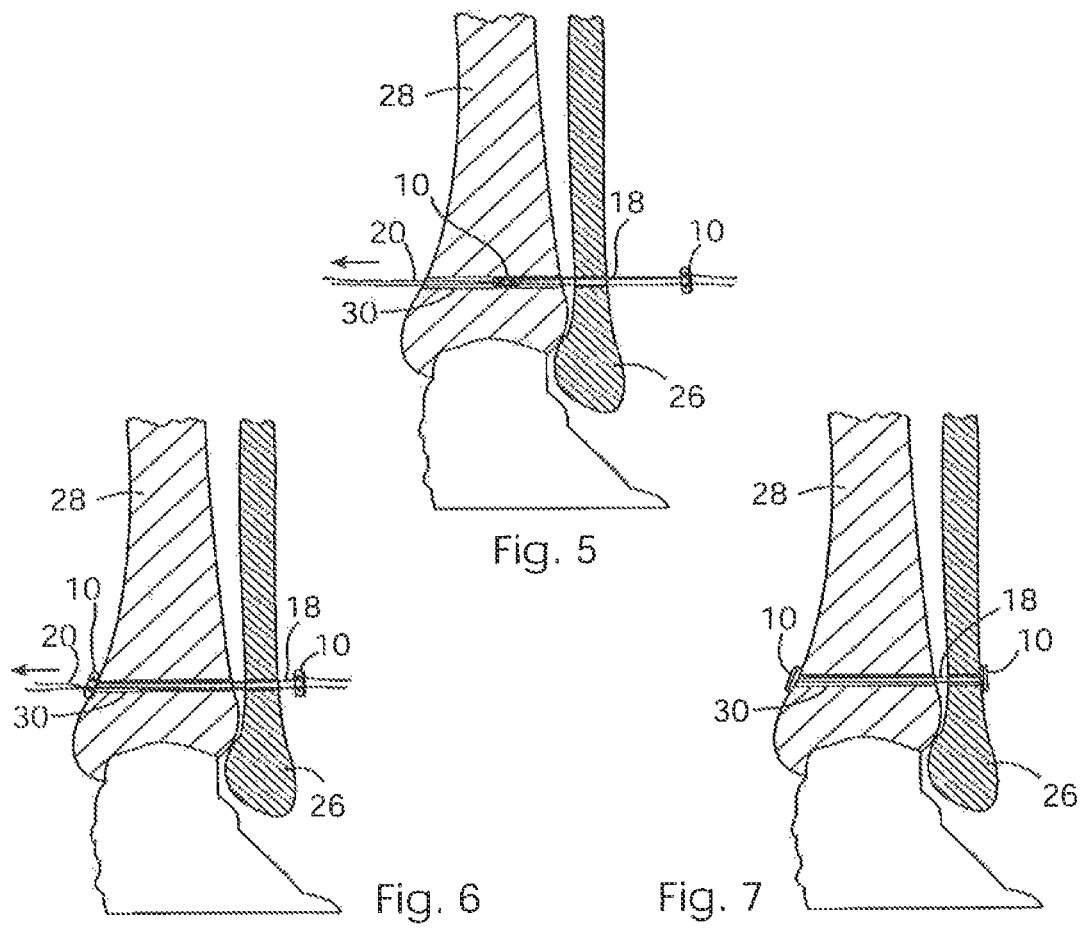

APPARATUSES AND METHODS FOR FIXATION OF ANKLE SYNDESMOSIS OR ACROMIOCLAVICULAR JOINT DISLOCATIONS OF THE SHOULDER

CROSS-REFERENCE TO RELATED APPLICATIONS

This application is continuation of U.S. application Ser. No. 13/970,269, filed Aug. 19, 2013, which is a divisional of U.S. application Ser. No. 11/482,038, filed Jul. 7, 2006, now U.S. Pat. No. 8,512,376, which claims the benefit of U.S. Provisional Application No. 60/697,125 filed on Jul. 7, 2005, and which is a continuation-in-part of U.S. application Ser. No. 10/233,122, filed Aug. 30, 2002, now U.S. Pat. No. 7,235,091, which claims priority under 35 U.S.C. § 119 to IE S2002/0504, filed Jun. 20, 2002.

The entire disclosures of all of the above priority applications are incorporated herein by reference.

FIELD OF THE INVENTION

The present invention relates to an apparatus and a method for fixation of ankle syndesmosis.

BACKGROUND OF THE INVENTION

Ankle syndesmosis disruptions are usually caused by severe external rotation ankle injuries. Surgery is recommended to reduce and internally fix the diastasis to prevent lateral talar shift, which could otherwise lead to post-traumatic arthrosis. Such surgical treatment usually involves tibio-fibular transfixation using a syndesmosis screw as recommended by the A.O. group (Arbeitsgemeinschaft für Osteosynthesefrage (Association for the Study of Internal Fixation)). Disadvantages of syndesmosis screw fixation include the need for a second operation for implant removal; implant fatigue and breakage; and loss of diastasis reduction following implant removal. Furthermore, prolonged non-weight bearing to avoid implant breakage prior to removal may cause further morbidity. In addition, studies have shown ligament healing to be inhibited by full immobilisation.

Movement of the distal fibula relative to the tibia is seen in normal ankle motion. Rigid fixation of the ankle syndesmosis, therefore, prevents normal physiological movement, until the rigid fixation device is removed, loosens or breaks.

Various methods of syndesmosis fixation have been studied before, including bioabsorbable implants (Thordarson D B, Hedman T P, Gross D, Magre G. "Biomechanical evaluation of polylactide absorbable screws used for syndesmosis injury repair" Foot Ankle Int 1997; 18: 622-7) and flexible implants (Miller R S, Weinhold P S, Dahners L E. "Comparison of tricortical screw fixation versus a modified suture construct for fixation of ankle syndesmosis injury: a biomechanical study" J Orthop Trauma 1999; 13: 39-42; Seitz W H Jr, Bachner E J, Abram L J, Postak P, Polando G, Brooks D B, Greenwald A S. "Repair of the tibiofibular syndesmosis with a flexible implant" J Orthop Trauma 1991; 5: 78-82). Seitz used a suture-button fixation using a large polyethylene button, as is commonly used for tendon repair pull-out sutures and a No. 5 braided polyester suture. Seitz's operative technique involved opening both the medial and lateral sides of the ankle. On biomechanical testing, failure occurred through the polyethylene button at an average of 20 kg of tension, and through the suture at 28 kg. Clinical testing in 12 patients showed good results, one patient having a symptomatic medial button. Buttons were routinely removed at 8 to 12 months, and were all found to be intact. Miller compared a modified suture construct against tricortical screw fixation at 2 cm and 5 cm above the ankle mortise. This method also required opening both the medial and lateral sides of the ankle. No. 5 braided polyester suture was looped through two holes drilled across the distal tibia and fibula. Similar results were seen for the suture and screw fixations, with a better holding strength for both groups at 5 cm.

It is an object of the present invention to overcome the problems associated with the prior art, whilst permitting normal physiological movement of the fibula relative to the tibia.

SUMMARY OF THE INVENTION

A method of ankle syndesmosis repair according to an exemplary aspect of the present disclosure includes, among other things, drilling a hole through a fibula and a tibia of an ankle joint, pulling a first button device through the hole using a pull-through suture until the first button device exits on a medial side of the tibia, flipping the first button device so it rests against a medial cortex of the tibia, and positioning a second button device at a lateral side of the fibula.

In a further non-limiting embodiment of the foregoing method, the method includes reducing a fracture of the fibula prior to drilling the hole.

In a further non-limiting embodiment of either of the foregoing methods, pulling the first button device includes connecting the first button device to a suture passing instrument with the pull-through suture and inserting the suture passing instrument through the hole to advance the first button device horizontally through the hole.

In a further non-limiting embodiment of any of the foregoing methods, flipping the first button device includes applying traction to the pull-through suture while applying counter-traction to a flexible coupling connected to the first button device until the first button device pivots from a position generally parallel to the hole to a position generally transverse to the hole.

In a further non-limiting embodiment of any of the foregoing methods, a flexible coupling is connected to the first button device and the second button device.

In a further non-limiting embodiment of any of the foregoing methods, the flexible coupling includes a suture that is double looped through the first button device and the second button device.

In a further non-limiting embodiment of any of the foregoing methods, positioning the second button device includes tightening down the second button device on the lateral side of the fibula by applying traction to a free end of a flexible coupling connected to each of the first button device and the second button device.

In a further non-limiting embodiment of any of the foregoing methods, the first button device and the second button device each include at least one aperture.

In a further non-limiting embodiment of any of the foregoing methods, pulling the first button device includes passing an elongated pull-through device that is connected to the pull-through suture through the hole.

In a further non-limiting embodiment of any of the foregoing methods, the method includes reducing a syndesmosis disruption prior to performing the drilling, pulling, flipping and positioning steps.

A method for internal fixation of an acromioclavicular joint dislocation of a shoulder according to another exemplary aspect of the present disclosure includes, among other things, drilling a hole through a first bone and a second bone of a shoulder joint, passing a first device through the hole, flipping the first device so it rests against a surface of the first bone, and positioning a second device against the second bone.

In a further non-limiting embodiment of the foregoing method, a flexible coupling is connected to the first device and the second device.

In a further non-limiting embodiment of either of the foregoing methods, the flexible coupling includes a suture that is double looped through the first device and the second device.

In a further non-limiting embodiment of any of the foregoing methods, passing the first device includes passing an elongated device that is connected to the first device through the hole.

In a further non-limiting embodiment of any of the foregoing methods, the first device is oblong and the second device is round.

In a further non-limiting embodiment of any of the foregoing methods, one of the first bone and the second bone is a clavicle and the other of the first bone and the second bone is a coracoid process.

These and other features and advantages of the present invention will become apparent from the following description of the invention that is provided in connection with the accompanying drawings and illustrated embodiments of the invention.

BRIEF DESCRIPTION OF THE DRAWINGS

The apparatuses, methods and buttons of the present invention are illustrated with respect to the following drawings:

FIGS. 3-7 illustrate, in sequence, the steps of a method according to the second aspect of the present invention;

FIG. 14 b illustrates the mobile positioning of the washer against an arcuate undersurface of the screw-head of a bone anchor;

DETAILED DESCRIPTION

The present invention provides minimally invasive, flexible fixation of the ankle syndesmosis whilst resisting tibio-fibular diastasis. It allows physiological micromotion at the ankle syndesmosis. There is no need for routine removal of the implant and its use should enable patients to weight-bear at an earlier stage.

The present invention is indicated for use in the fixation of ankle syndesmosis tibio-fibular diastasis (splaying apart). These are typically seen in Weber C-type ankle injuries, caused by severe pronation-external rotation forces. The fibula is fractured above the level of the syndesmosis. A medial ankle injury (malleolar fracture or deltoid ligament rupture) is also usually present. Reduction and fixation of the ankle syndesmosis is necessary to prevent lateral talar shift, which can lead to premature ankle osteo-arthritis.

Figure 1:
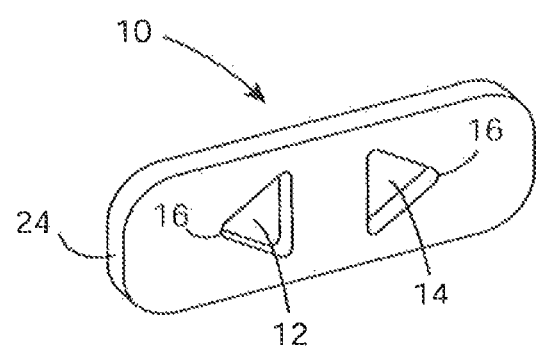
FIG. 1 shows a perspective view of a button of the present invention.
Figure 2:
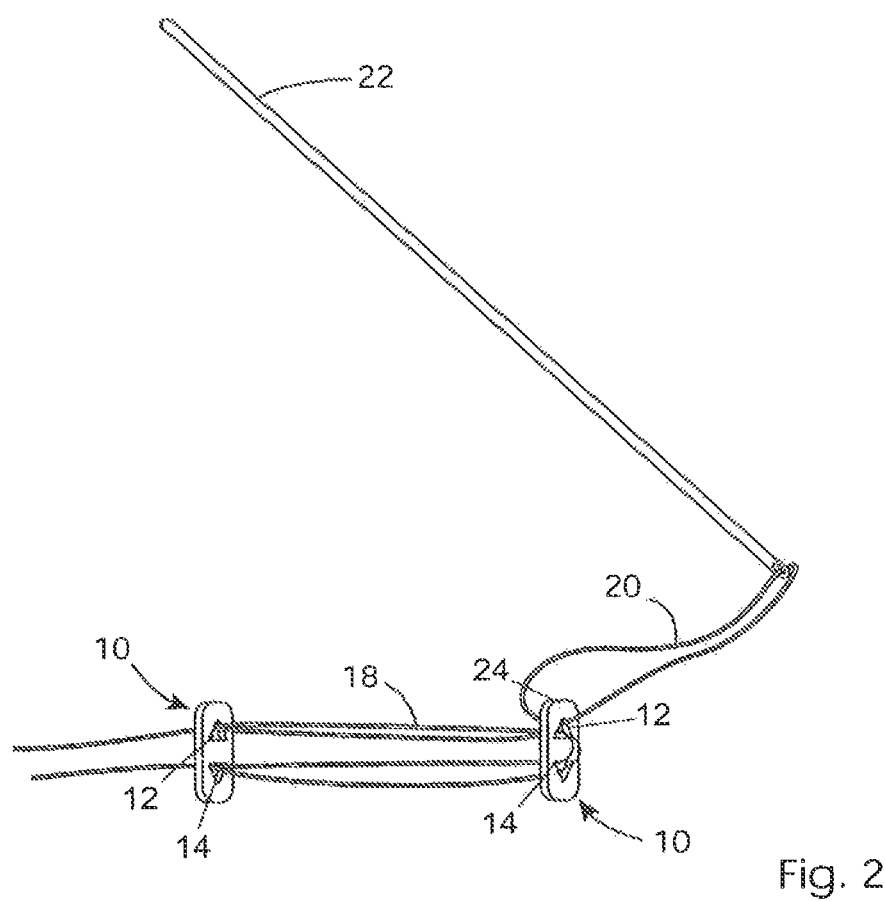
FIG. 2 shows a perspective view of the kit of parts comprising an apparatus of the present invention.

Thus, referring to the accompanying drawings, the apparatus of the present invention comprises a pair of buttons 10, which, in the preferred embodiment illustrated are 9 mm by 3.5 mm in dimension, more particularly in length and width respectively. The buttons 10 are preferably formed from titanium or stainless steel, although it will of course be appreciated that any other suitable material could be used, in particular any suitable bioabsorbable material. The pair of buttons 10 each have a first aperture 12 and a second aperture 14 which, in the preferred embodiment illustrated, are triangular in shape, each of the first and second apertures 12, 14 having an apex 16, the respective apices 16 preferably being directed away from one another and being located substantially about a longitudinal mid-line of the button 10. Referring in particular to FIG. 2, the pair of buttons 10 are secured or pre-threaded together by means of a flexible coupling in the form of first suture 18, preferably of no. 5 braided polyester, which is double looped through the first and second apertures 12, 14 of the pair of buttons 10, as will be described in greater detail hereunder. It will be readily understood however that any suitable material could be used for the first suture 18. A straight needle 22 with a second (pull-through) suture 20, again of any suitable material, is also looped through either the first or second aperture 12, 14 of one of the pair of buttons 10, hereinafter referred to as the leading (or first) button 10. The needle 22 is preferably 100 mm in length. In the embodiment illustrated in FIG. 2, the second suture 20 is looped through the first aperture 12 of the first button 10.

TABLE 1

Apparatus/Button of the Present Invention

| | |
|---|---|
| Button 10 overall dimensions: | 9.0 mm (length) × 3.5 mm (width) × 1.5 mm (thickness) |
| Basic shape: | Oblong in plan shape, with chamfered or rounded corners and edges - this reduces the chance of the button 10 being palpated under the skin and, in addition, eases the passage of the first button 10 through a drill hole 30 as will be explained hereinafter. |

TABLE 1-continued

Apparatus/Button of the Present Invention

| | |
|---|---|
| Button 10 material: | Preferably titanium or stainless steel |
| Button apertures 12, 14: | 2 apertures 12, 14 (triangular in plan shape) |
| Aperture 12, 14 dimensions: | 2 mm base × 2 mm perpendicular height (equilateral triangle with chamfered corners), 1 mm distance between first and second apertures |
| Syndesmosis suture 18 (first suture): | Number 5 braided polyethylene suture, looped twice through the first and second apertures 12, 14 of the first and second buttons 10, leaving the two free ends of suture 18 free for tying. |
| Pull-through needle 22: | 100 mm long straight needle 22 with pull-through (or second) suture 20 attached. |
| Pull-through suture 20: | Minimum 0-strength suture 20 looped through the aperture 12 of the first button 10, the second suture 20 being secured to the needle 22. |

In the present embodiment, leading and trailing edges of the button 10 of the present invention are substantially symmetrical, although it will be appreciated that this is not a requirement of the present invention. Specifically, the leading edge 24 of the button 10 of the present invention should be blunt and should have a width sufficient to reduce the possibility that the leading edge 24 of the first button 10 follows the second or pull through suture 20 through the intact medial skin or to catch or skewer any soft tissue structures between the bone and the medial skin, as will be described in detail hereinafter.

The button 10 of the third aspect of the present invention may be provided with apertures 12, 14 which are countersunk (not illustrated) so as to allow easier threading passage of the first and second sutures 18, 20. Care needs to be taken in such countersinking, to avoid compromising the mechanical strength of the first and second apertures 12, 14 of the button 10 of the present invention.

The first suture 18 used in the apparatus of the present invention can be of any material, which is suitable for this purpose, whether absorbable or non-absorbable, provided it is sufficiently strong. A number 5—strength braided polyester (ETHIBOND—Trade Mark) suture is preferred. This is a non-absorbable suture which knots easily without slipping.

The second suture 20 used in the present invention can be of any material which is suitable for this purpose, provided it is of at least 0—strength.

The pull through needle 22 can be of any dimensions, provided it is long enough to span the ankle. Its tip can be either "taper cut" or "cutting".

Set-Up

The patient is positioned supine on a radiolucent operating table (not shown). Intra-operative fluoroscopy is necessary during the procedure. The patient and all theatre personnel should be adequately protected for x-ray radiation. A sandbag (not shown) is placed under the ipsilateral buttock to facilitate internal rotation of the leg. Antibiotic prophylaxis and the use of a tourniquet are recommended.

Instrumentation

An A.O. small fragment set (or equivalent) should be used for fracture osteosynthesis. The 3.5 mm drill bit is required for drilling the hole 30 through both the fibula 26 and tibia 28, for the first button 10 and first and second sutures 18, 20 to pass through, as illustrated in FIGS. 3 to 7. This corresponds to the 3.5 mm drill bit which is part of the small fragment set routinely used to internally fix ankle fractures. It will, of course, be appreciated that the diameter of the hole 30 must be sufficient to permit the first button 10 to be pulled, lengthways, therethrough.

Fracture Fixation

Osteosynthesis should be undertaken according to A.O. principles of internal fixation. It is recommended that fractures (not shown) in the lower half of the fibula 26 should be fixed. High fibular fractures (Maisonneuve injury) can be managed by addressing the syndesmosis diastasis only. Care should be taken not to injure the superficial peroneal nerve during the lateral approach to the fibula 26; the nerve passes posteriorly to anteriorly as it pierces the deep fascia. A one-third tubular plate usually provides sufficient stability and can be contoured easily to sit on the bone. The use of a lag screw for fracture compression is rarely required, once fibular length and rotation have been corrected.

Syndesmosis Reduction

The syndesmosis is reduced by internal rotation of the ankle, at around 30° of plantar flexion. This does not result in an over-tightening of the syndesmosis. Reduction should be confirmed using the image intensifier.

Drilling

All four cortices are drilled from the open lateral side using the 3.5 mm drill bit. The drill (not shown) should be angled at 30° upwards from the horizontal, at a distance of 2-3 cm above the ankle joint. Placing a finger on the medial aspect of the leg can help with aiming and feel when the drill has passed through. The drill hole 30 may go through one of the holes of a one-third tubular plate (not shown), if needed. To ensure accurate placement, drilling should be performed under image intensifier control.

Button Placement

The long straight needle 22 with pull-through, second suture 20 is passed through the drill-hole 30 and out the intact medial skin (see FIG. 3). The pull-through suture 20, which engages the apex 16 of the first aperture 12 of the first button 10, can now advance the first or leading button 10, substantially horizontally through the drill hole 30 (FIGS. 4 & 5). Engagement of the second suture 20 in the apex 16 ensures that the second suture 20 is located adjacent the longitudinal mid-line of the first button 10 so that the second suture 20 stays central in the first aperture 12. Once this first button 10 has exited the medial tibia 28, the angle of traction on the pull-through, or second suture 20 is changed and counter-traction is exerted on the first suture 18, in order to flip (pivot) and engage the first button 10 against the medial tibial cortex (FIG. 6). Once the first button 10 is anchored, the pull-through (second) suture 20 can be cut and removed. The trailing or second button 10 is tightened down on the lateral side by further traction on the free ends of the first suture 18 and should be tied hand tight (FIG. 7). This will further squeeze the syndesmosis but will not over-tighten it.

Post-Operative Management

Following wound closure, the ankle should be placed in either a well-padded below-knee cast or backslab, ensuring the ankle is kept in a neutral position. The patient should be kept non-weight bearing for the first two weeks, and then allowed to partial weight-bear (50%) from two to six weeks in cast, depending on fracture stability. Full weight bearing can be allowed out of cast at six weeks.

Implant Removal

Routine removal of the suture-button construct is not required. If, for any reason, it needs to be removed, this can be performed simply by small incisions over the medial and lateral buttons 10, cutting the first suture 18 as it loops through the button 10 and removing the pair of buttons 10 and the first suture 18.

Example 1

Phase One aims to reproduce a cadaver model of a syndesmosis injury, with a medial deltoid ligament rupture. An intact fibula simulates an anatomically fixed fracture. Phase two compares the suture-button versus conventional A.O. screw fixation following total intraosseous membrane (IOM) division, in a model resembling a Maisonneuve injury.

Material and Methods

Sixteen embalmed cadaver legs (eight pairs) were used. For each leg (not shown), the tibia and foot were fixed to a customised jig using Steinman pins. The foot was fixed to a mobile footplate so that the centre of rotation was directly under the centre of the ankle joint. External rotation moment was applied tangential to the centre of rotation at a radius of 25 cm. 1 kg of weight used therefore corresponds to approximately 2.5 Newton-meters of torque. The syndesmosis was exposed via an antero-lateral approach. Marker pins were placed in the tibia and fibula at the level of the syndesmosis to aid clinical and radiographic measurements. Clinical measurements were made using vernier calipers. In order to reduce bias, x-rays received a coded label to help blind subsequent review. The distance between the tips of the marker pins was measured on the mortise view x-ray. The stress lateral view was found to be less reliable, due to lack of reproducibility.

A 5 kg (12.5 Nm) load was used for all phase one measurements. Following baseline readings, the medial deltoid and syndesmotic ligaments were divided. Measurements of diastasis were taken following 5 cm, 10 cm and total intraosseous membrane division.

In phase two, left and right ankles were randomised to receive a suture-button 10 (4 mm×11 mm; the button being a conventional button marketed by Smith & Nephew Inc. under Endo-Button®) or A.O. standard (4.5 mm) screw fixation (not shown). In both groups, the syndesmosis was first reduced by internal rotation of the footplate. A hole was then drilled from lateral to medial, at 30° anterior to the horizontal, 2 cm superior to the ankle joint.

In the suture-button group of the present invention, a 4 mm drill hole 30 was drilled through all four cortices. The no. 5 braided polyester first suture 18 was looped twice through first and second apertures 12, 14 of the first and second buttons 10. The second suture 20 was threaded through the first aperture 12 of the first button 10 and also through the needle 22. This needle 22 was passed into the drill hole 30 from the lateral side and out through the intact medial skin. Using the leading pull-through suture 20, the first button 10 was advanced horizontally along the drill hole 30 until it has exited the medial tibial cortex. Using the leading pull-through second suture 20, whilst maintaining traction on the braided polyester first suture 18, the first button 10 was flipped to engage and anchor against the medial tibial cortex. The second suture 20 was then pulled out. The second button 10 was tightened against the lateral fibular cortex by further manual traction on the braided polyester first suture 18. The first suture 18 was securely tied over the second button 10 when flush with the lateral fibular cortex. The progress of the first button 10 may be followed intra-operatively using an x-ray image intensifier (not shown), if available.

In the comparative group (A.O. screw), a 3.2 mm drill hole was drilled through all four cortices. The hole was measured, tapped and an A.O. 4.5 mm cortical screw inserted to engage all four cortices, maintaining the reduction of the syndesmosis, without compression.

Measurements of syndesmosis diastasis were taken both under direct vision and radiographically at increasing external rotation torques. Torque loads were increased in increments of 1 kg, to a maximum of 8 kg or until fracture or implant failure. In four ankles (two per group), fixations were also tested at 5 cm above the ankle joint, having removed the fixations at 2 cm, in order to determine the optimum level of fixation placement.

Results

Figure 8:
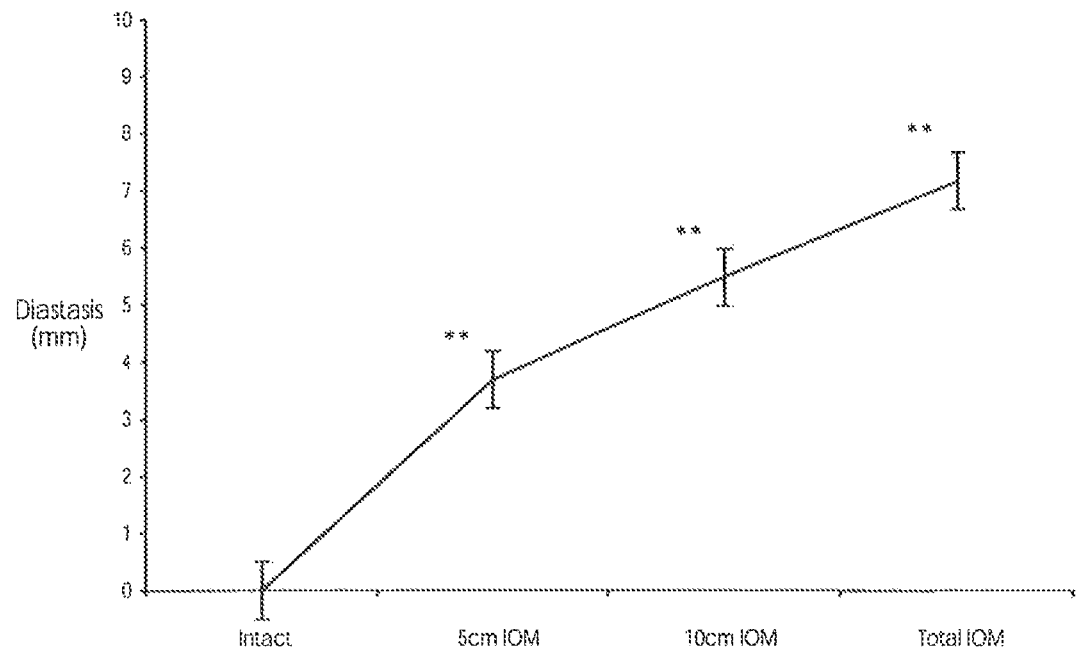
FIG. 8 shows the mean diastasis in millimeters above the baseline with increasing intraosseous membrane (IOM) division with no fixation and a 5 kg (12.5 Nm) load, in which the error bars represent standard deviation and the use of ** indicates p<0.001.

In phase one, the mean values of the measured diastasis above the baseline value at 5 cm, 10 cm and total intraosseous (IOM) division under 5 kg (12.5 Nm) load were 3.7 mm, 5.5 mm and 7.2 mm, respectively (see FIG. 8). Each value showed significant increase in diastasis compared to the previous measurement, (p<0.001, unpaired t-test). Radiographic measurements were less reliable than direct clinical measurements, but gave a similar picture.

Figure 9:
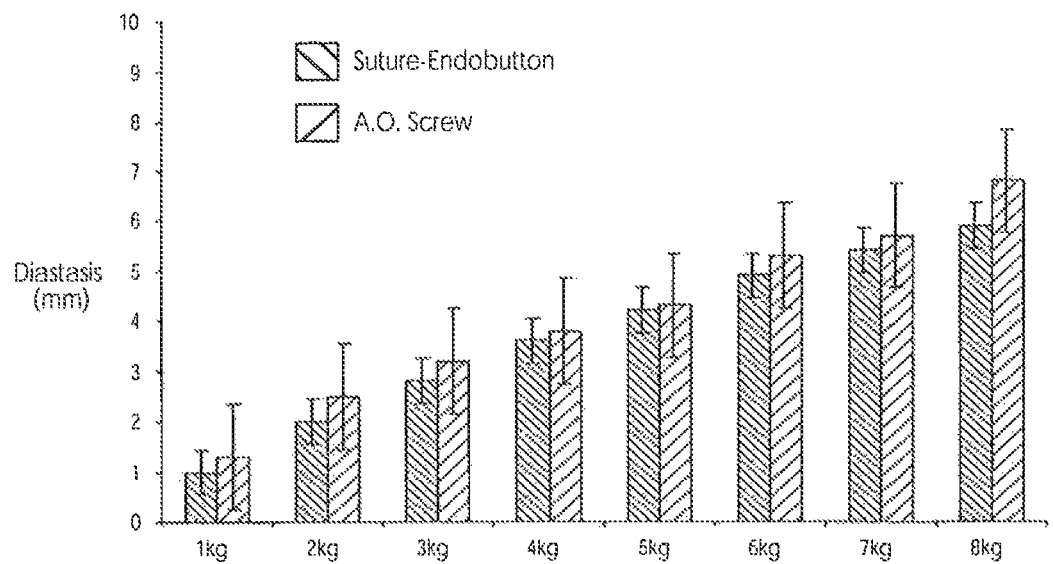
FIG. 9 shows the apparatus, method and button of the present invention, when compared with A.O. screw fixation at 2 cm with increasing torque load following total IOM division and, again, the error bars represent standard deviation.

In phase two, there was a gradual diastasis with increasing torque load in both groups, which was probably due to the quality of the bone. The mean diastasis from baseline for the suture-Endo-Button® and the A.O. screw groups for torque loads increasing at 1 kg intervals, up to 8 kg, are shown in Table 2. These differences were not statistically significant (p=0.7, unpaired t-test, FIG. 9).

The apparatus and method of the present invention did give a more consistent performance, though. The distribution of standard deviations for A.O. screw fixation was 0.64 mm higher than that for the apparatus and method of the present invention (95% C.I. 0.46 to 0.84, Hodges-Lehmann estimation of shift).

There were no implant failures in either group. There were two fibular fractures in the A.O. screw group, prior to reaching the 8 kg load (5 kg, 8 kg). Only measurements prior to fracture were used for analysis. By comparison, there was one fibular fracture in the group of the present invention (8 kg). Comparing fixation placement at 2 cm versus 5 cm showed no significant difference (Table 2).

Discussion

The cadaver model in this study was tested using a jig (not shown) generating external rotation torque, which reproduces the mechanism of syndesmosis injury and, therefore, reflects the clinical situation.

Syndesmosis diastasis is seen with increasing intraosseous membrane division, under an external rotation torque load. This corroborates the findings of previous studies, showing a significantly larger diastasis with greater intraosseous membrane division.

Regarding the level of placement of the fixation, there was a trend towards better fixation at 2 cm, although only a small sample size was tested (Table 2).

Flexible fixation gives a more physiological end-result, allowing for micromotion at the distal tibio-fibular joint. Implant fatigue or breakage is less likely and routine removal is not essential. This avoids the complication of loss of reduction following removal of fixation. Earlier weight-bearing may be allowed, depending on the overall fracture configuration.

The advantages of the suture-button technique are that it is simple, flexible, minimally invasive as the medial side does not need to be opened, and has given a consistent performance on biomechanical testing. Clinical testing of the suture-button in ankle injuries that require reduction and fixation of a syndesmosis diastasis is recommended.

TABLE 2

Mean diastasis in millimetres above baseline post-fixation, under increasing torque load. 1 kg is equivalent to 2.5 Nm of torque. (Standard deviations are in parentheses.)

|  | Button [2 cm] n = 8 | A.O. Screw [2 cm] n = 8 | Button [5 cm] n = 2 | A.O. Screw [5 cm] n = 2 |
| --- | --- | --- | --- | --- |
| 1 kg | 1.0 mm (0.41) | 1.3 mm (0.58) | 2.5 mm | 2.0 mm |
| 2 kg | 2.0 mm (0.00) | 2.5 mm (0.87) | 3.0 mm | 3.0 mm |
| 3 kg | 2.8 mm (0.29) | 3.2 mm (1.04) | 3.5 mm | 4.0 mm |
| 4 kg | 3.6 mm (0.48) | 3.8 mm (1.25) | 4.0 mm | 5.0 mm |
| 5 kg | 4.2 mm (0.57) | 4.3 mm (1.30) | 5.0 mm | 5.5 mm |
| 6 kg | 4.9 mm (0.53) | 5.3 mm (1.04) | 6.0 mm | 6.0 mm |
| 7 kg | 5.4 mm (0.53) | 5.7 mm (1.25) | 6.5 mm | 7.0 mm |
| 8 kg | 5.9 mm (0.53) | 6.8 mm (1.05) | 7.0 mm | 8.0 mm |

Example 2

Patients with Weber C ankle fractures who had suture-button fixation, were compound with a cohort of patients who had syndesmosis screw fixation.

Methods 8 patients had suture-button fixation. The buttons used in Example 2 were conventional buttons supplied by Smith & Nephew Inc. and marketed under Endo-Button®. A retrospective cohort of 8 patients with similar Weber C fractures, treated using syndesmosis screw fixation, were recalled for clinical and radiological evaluation. Outcome was assessed using the American Orthopaedic Foot and Ankle Surgeons (AOFAS) score on a 100-point scale.

Results

Patients with screw fixation had a mean AOFAS score of 79 (range: 61-100) at an average follow-up of four months (range: 3-6 months). The suture-button group had a mean score of 92 (range: 76-100) at three-month review (p=0.02, unpaired t-test). Six of the screw group required further surgery for implant removal, compared to none of the suture-button group (p=0.007, Fisher's exact test).

CONCLUSION

Patients treated using the suture-button 10 regained a better functional outcome, within a shorter time frame. The technique is minimally invasive, as the medial side is not opened, and allows tibio-fibular micromotion whilst resisting diastasis. The need for secondary surgery for implant removal is significantly lessened. The suture-button technique may become the gold standard for syndesmosis diastasis injuries.

The present invention also provides minimally invasive, flexible fixation of the AC joint dislocation by resisting superior migration of the clavicle with respect to the coracoid process. It allows physiological micromotion at the AC joint. There should be no need for routine removal of the implant.

The present invention is indicated for use in the fixation of AC joint dislocation. These are typically seen in Rockwood type III AC joint dislocations, usually caused by severe downward blunt trauma to the point of the shoulder, or acromium. Typically, the clavicle is upwardly displaced as a result of the injury because of disruption to the AC and coracoclavicular ligaments. Reduction and fixation of displaced AC joint dislocations are necessary to prevent painful deformity and loss of function.

Figure 10:
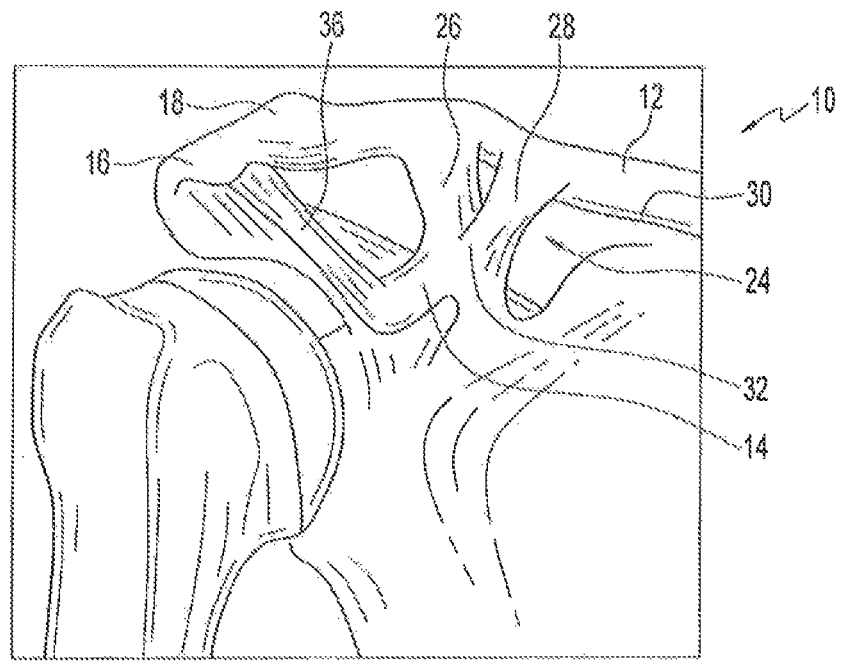
FIGS. 10 and 10 a show an anterior view and a schematic view, respectively, of a normal acromioclavicular joint.
Figure 11:
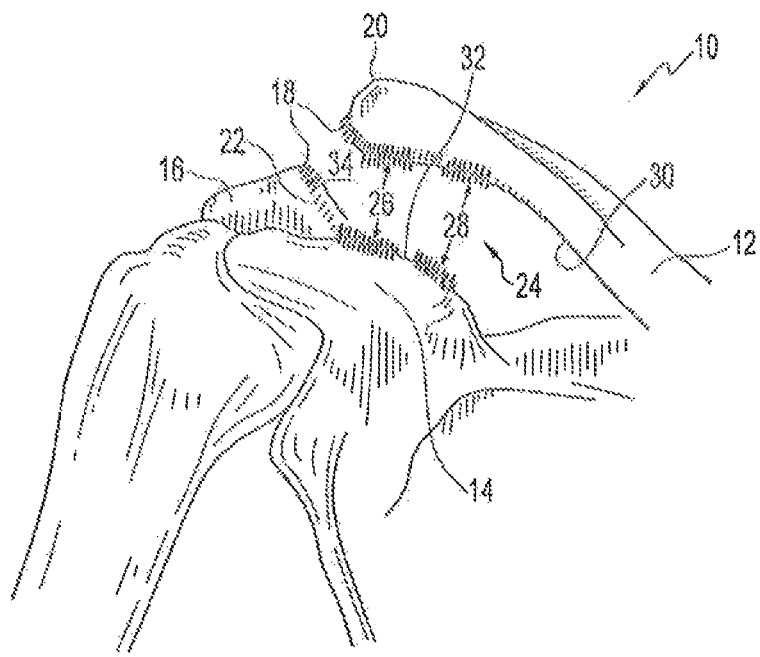
FIGS. 11 and 11 a show an anterior view and a schematic view, respectively, of a Rockwood Type III acromioclavicular joint dislocation, with superior migration of the clavicle with respect to the acromium.
Figure 10A:
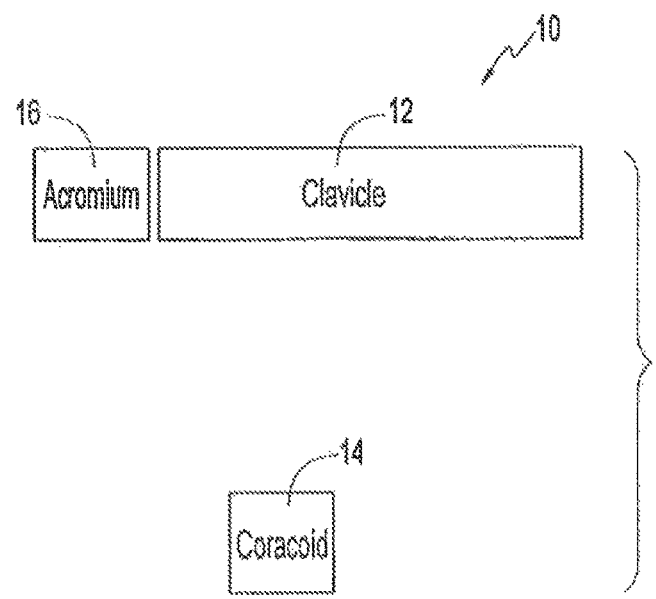
Figure 11A:
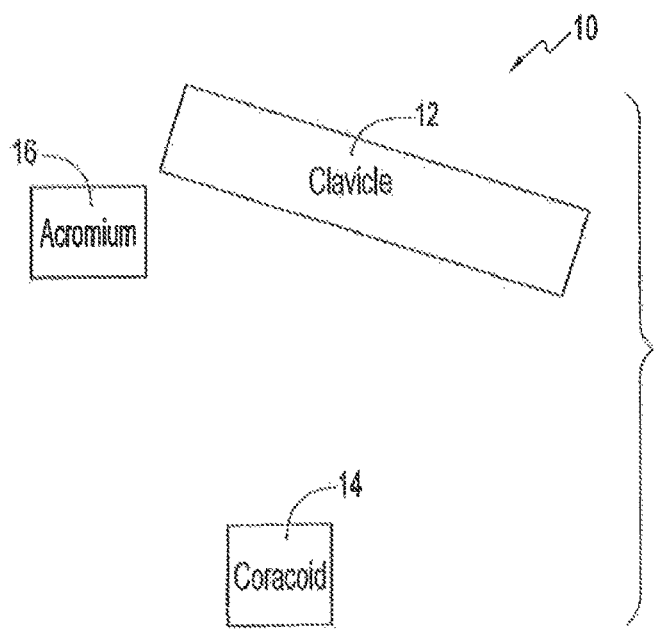

FIGS. 10 and 10a show anterior and schematic views of a normal shoulder 10. FIGS. 11 and 11a show anterior and schematic views of a shoulder 10 that has suffered a Rockwood type III AC joint dislocation injury.

Referring to FIGS. 10 and 11, the structure of a shoulder 10 relevant to a Rockwood type III dislocation injury includes the clavicle 12, the coracoid process 14 and the acromium 16. The acromium 16 and the clavicle 12 are connected by the acromioclavicular ligament 18. The acromioclavicular ligament 18 extends from the lateral end 20 of the clavicle 12 to the medial surface 22 of the acromium 16. The coracoid process 14 is connected to the clavicle 12 by the coracoclavicular ligaments 24, which comprise the trapezoid ligament 26 and the conoid ligament 28. The coracoclavicular ligaments 24 extend from the inferior surface 30 of the clavicle 12 to the superior surface 32 of the coracoid process 14.

A Rockwood type III AC joint dislocation is characterized by the disruption of the AC and the coracoclavicular ligaments 18, 24, respectively. As shown in FIGS. 11 and 11a, the clavicle 12 separates from, and moves away from, the coracoid process 14 and the acromium 16, accompanied by disruption of the coracoclavicular and the AC ligaments 18, 24, respectively. The acromioclavicular joint 34 (FIG. 11) is dislocated and the clavicle 12 is relatively displaced upwardly. The coraco-acromial ligament 36 (FIG. 10) is not impacted in the type III shoulder dislocation.

Repair of the type III shoulder dislocation according to the present invention is an out-patient procedure performed with a general anesthetic. The procedure is done with the patient lying supine on the operating table, preferably in the "deck-chair" position to allow the surgeon full access to the affected shoulder.

Figure 12:
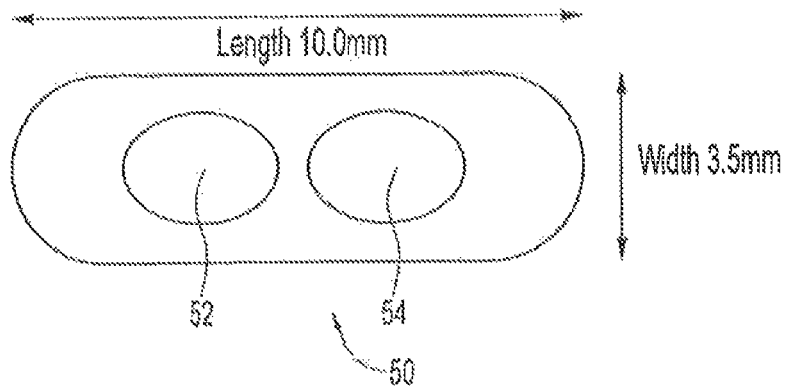
FIG. 12 shows a plan view of a first or second suture anchor in the form of a button of the present invention.

Referring to FIG. 12, the apparatus of the present invention comprises a first or second suture anchor in the form of a button 50, which, in the embodiment illustrated, is about 10.0 mm in length by about 3.5 mm in width. The button 50 is preferably formed from titanium or stainless steel, although it will be appreciated that any other suitable material could be used, in particular any suitable bioabsorbable material. The button 50 has a first aperture 52 and a second aperture 54 which, in the embodiment illustrated, are oblong in shape, the longitudinal mid-line of each of the first and second apertures 52, 54 being located substantially about a longitudinal mid-line of the button 50.

Figure 13:
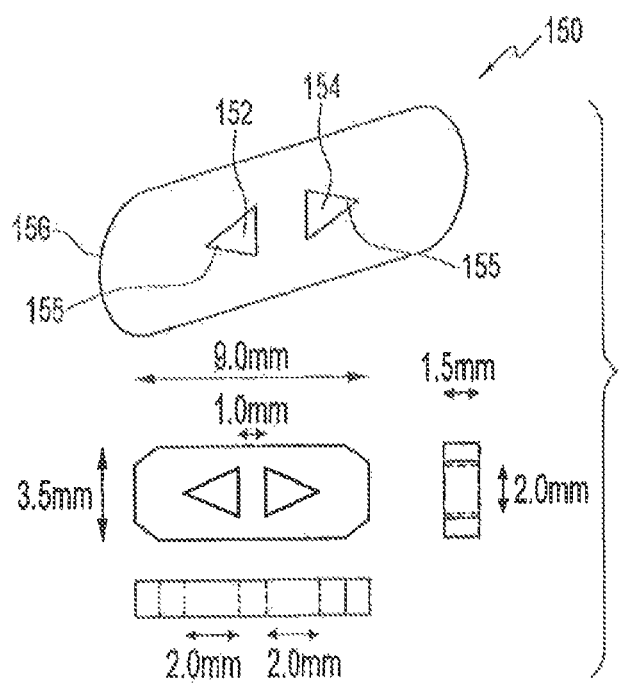
FIG. 13 shows perspective, plan and sectional view of an alternative embodiment of a button according to the invention.

Referring to FIG. 13, there is illustrated an alternative first or second suture anchor, generally indicated as 150. In the illustrated alternative embodiment, the button 150 is about 9.0 mm in length by about 3.5 mm in width, with a thickness of about 1.5 mm. The button 150 has first and second apertures 152 and 154, respectively. In the illustrated alternative embodiment, each of the apertures 152, 154 are triangular in shape, the respective apices 155 being directed away from each other and being located substantially about a longitudinal mid-line of the button 150.

Figure 14:
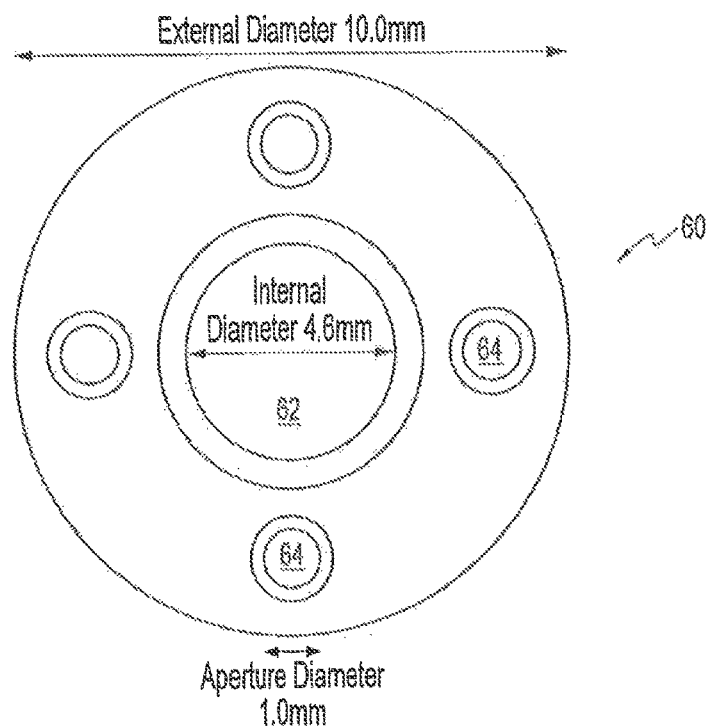
FIGS. 14 and 14 a show a plan and an undersurface view, respectively, of a first or second suture anchor in the form of a washer of the present invention.
Figure 14A:
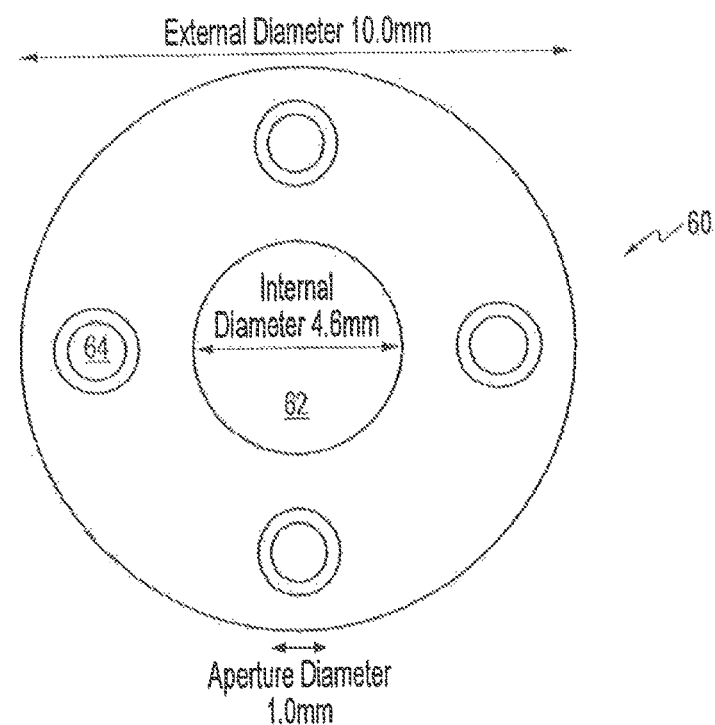

Reference is now made to FIGS. 14 and 14a which illustrate a first or second suture anchor in the form of a washer 60. In the illustrated embodiment, the washer 60 has an external diameter of about 10.0 mm. While the illustrated washer is disc-shaped, the washer is not so limited. The washer 60 is preferably formed from titanium or stainless steel although, as will be appreciated by those skilled in the art, any other suitable material, in particular any suitable bioabsorbable materials, may be used. The washer 62 also has at least two flexible coupling-locating apertures 64. In the illustrated embodiment, there are four apertures 64 circumferentially arranged about the aperture 62. In the illustrated embodiment, each of the apertures 64 has a diameter of about 1.0 mm. Each of the apertures 64 have beveled edges, above and below, while the aperture 62 has beveled edges above.

The washer 60 also has a substantially centrally located bone screw-retaining aperture 62. In the illustrated embodiment, the aperture 62 has a diameter of about 4.6 mm and the washer 60 is adapted to allow mobile positioning against an arcuate undersurface 69 of the head of the bone screw 68 (illustrated in FIG. 14 *b*).

Referring to FIGS. 14 and 14*a*, the washer 60 of the fourth aspect of the present invention is provided with a screw-retaining aperture 62 and at least two flexible coupling-locating apertures 64 which are preferably countersunk so as to allow easier threading passage of the flexible coupling 70 (not shown in FIGS. 14-14 *b*). Care needs to be taken in such countersinking, to avoid compromising the mechanical strength of the apertures 62, 64 of the washer 60.

Figure 15:
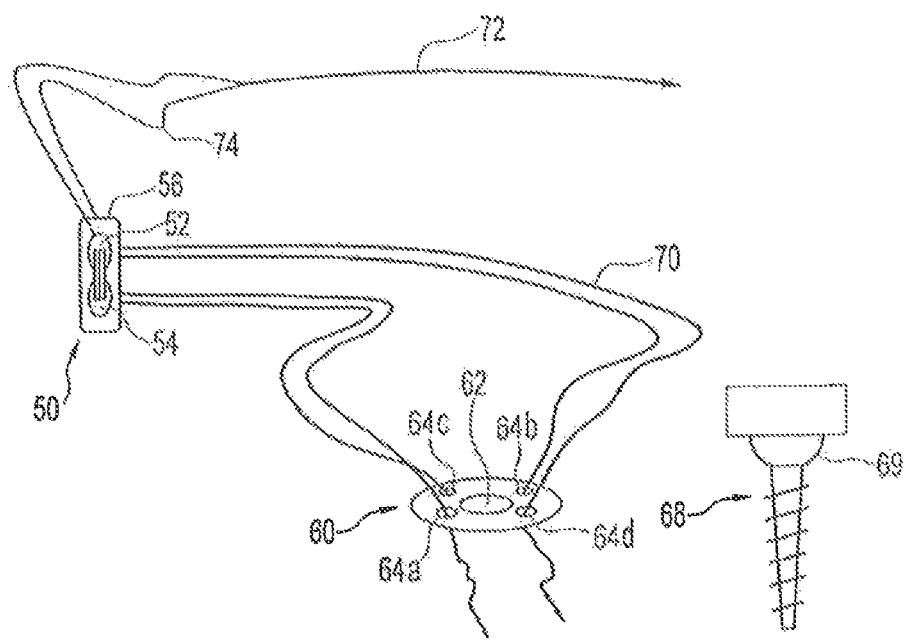
FIG. 15 shows a perspective view of the kit of parts comprising an apparatus of the present invention.

FIG. 15 illustrates the implant apparatus used for fixation of the AC joint dislocation. The button 50 and the washer 60 are secured or pre-threaded together by means of a flexible coupling in the form of first suture 70, preferably of number 5-strength braided polyester, which is double looped through the first and second apertures 52, 54 of the button 50 and the peripheral apertures 64 of the washer 60, as will now be described in greater detail. Specifically, the first suture 70 is fed through to aperture 64*a* of the washer 60; through the second and first apertures 54, 52 of the button 50; through the aperture 64*b*, under the washer 60 and back out the aperture 64*c*; through the second and first apertures 54, 52 of the button 50 again; and finally through the aperture 64*d* of the washer 60. A needle 72, which may be straight or curved, with a second, pull-through suture 74 is also looped through either the first or second apertures 52, 54 of the button 50. The second suture 74 is looped through the first aperture 52 of the button 50.

The first suture 70 used in the apparatus can be made from any material which is suitable for this purpose, whether absorbable or non-absorbable, provided it is sufficiently strong. A number 5-strength braided polyester (FIBER-WIRE®) suture is preferred. This is a non-absorbable suture which knots easily without slipping. The second suture 74 can be made from any material which is suitable for this purpose, and preferably should be at least 0-strength.

The pull through needle 72 can be of any dimensions, provided it is long enough to span the clavicle 12 or the coracoid process 14 of the shoulder 10. The needle 72 is preferably about 100 mm in length. The needle's body can either be straight or curved. The needle's tip can be either "taper cut" or "cutting."

In the present embodiment, leading and trailing edges of the button 50 are substantially symmetrical, although it will be appreciated that this is not a requirement of the present invention. Specifically, the leading edge 56 (illustrated in FIG. 15) of the button 50 should be blunt and should have a width sufficient to reduce the possibility that the leading edge 56 of the button 50 follows the second or pull-through suture 74 through the intact skin or to catch or skewer any soft tissue structures between the bone and the skin, as will be described in detail hereinafter.

Figure 14B:
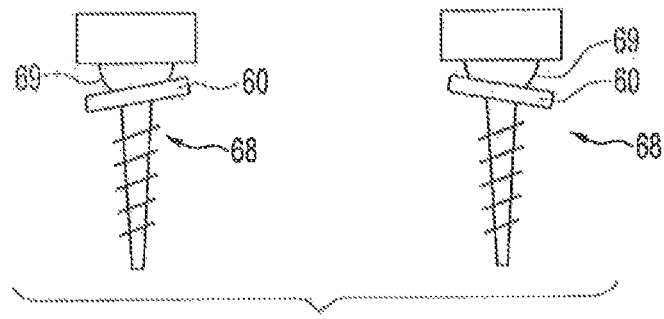

FIG. 15 also illustrates a bone screw 68 as part of the implant apparatus. The bone screw 68 is used for engaging the washer 60 with the coracoid process 14 (FIG. 16 *f*). As discussed below in detail and with reference to FIG. 14*b*, the bone screw 68 has an arcuate undersurface 69 for defining the movement of the washer 60 between the coracoid process 14 and the arcuate undersurface 69.

TABLE 3

| Apparatus/Button of FIGS. 12 and 15 | |
| --- | --- |
| Button 50 overall dimensions: | 10.0 mm (length) × 3.5 mm (width) × 1.5 mm (thickness) |
| Basic shape: | Oblong in plan shape, with chamfered or rounded corners and edges - this reduces the chance of the button 10 being palpated under the skin and, in addition, eases the passage of the button 50 through a drill hole as will be explained hereinafter. |
| Button 50 material: | Preferable titanium or stainless steel |
| Button apertures 52, 54: | Two apertures 52, 54 (oblong in plan shape) |
| Aperture 52, 54 dimensions: | 2 mm height × 3 mm length (oblong with chamfered edges), preferably 1 mm distance between first and second apertures |
| Suture 70 (first suture): | Number 5 strength braided polyester suture, looped twice through the first and second apertures 52, 54 of the button 50 and each of the four apertures 64 (64a, 64b, 64c, 64d) of the washer, leaving the two free ends of suture 70 free for tying adjacent the undersurface of the washer 60. |
| Pull-through needle 72: | 100 mm long straight, or curved, needle 72 with pull-through, or second suture 74 attached. |
| Pull-through suture 74: | Minimum 0-strength suture 74 looped through the aperture 52 of the button 50, the second suture 74 being secured to the needle 72. |

The following sets out the procedure, as shown in FIGS. 16 *a*-16 *f*, to be followed for Rockwood Type III dislocations. Surgeons skilled in the art will appreciate the modifications that might be needed in addressing Rockwood Type II and IV-VI dislocations.

Set-Up

The patient is positioned in a "deck-chair" position on the operating table (not shown). A sandbag (not shown) can be placed under the scapula to ease access to the shoulder region. A longitudinal or horizontal incision of about 5 cm is made on the skin, at the front of the shoulder, overlying the coracoid process 14 and the clavicle 12. The clavicle 12 and the superior surface of the coracoid process 14 are exposed by blunt dissection. As explained in detail below, if the clavicle hole 80 is to be drilled (FIG. 16*a*) from above and substantially downwardly through the clavicle 12, it will also be necessary to retract the skin about the clavicle 12, in order to expose the superior surface 33 of the clavicle 12.

Instrumentation

A 3.5 mm drill bit is required for drilling a hole 80 through the clavicle 12. A 2.5 mm drill bit is required for drilling a hole 82 into the base of the coracoid process 14 of the scapula (FIG. 16 *a*). It is not necessary that the drill holes 80, 82 be aligned with each other. In addition, it is not necessary, when the coracoclavicular interspace is reduced to normal, that the longitudinal axes of the respective drill holes 80, 82 be co-linear or even substantially parallel with each other.

Button Placement

Figure 16A:
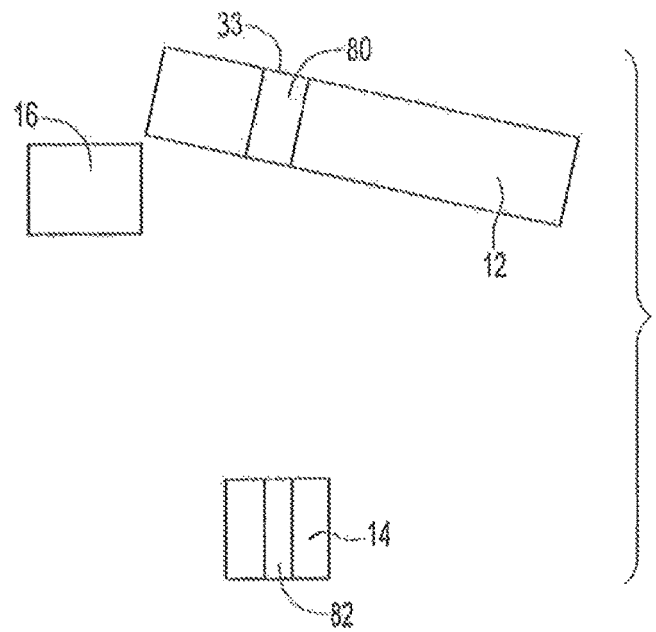
FIGS. 16 a-16 f illustrate, in sequence, the steps of a method according to the present invention.
Figure 16B:
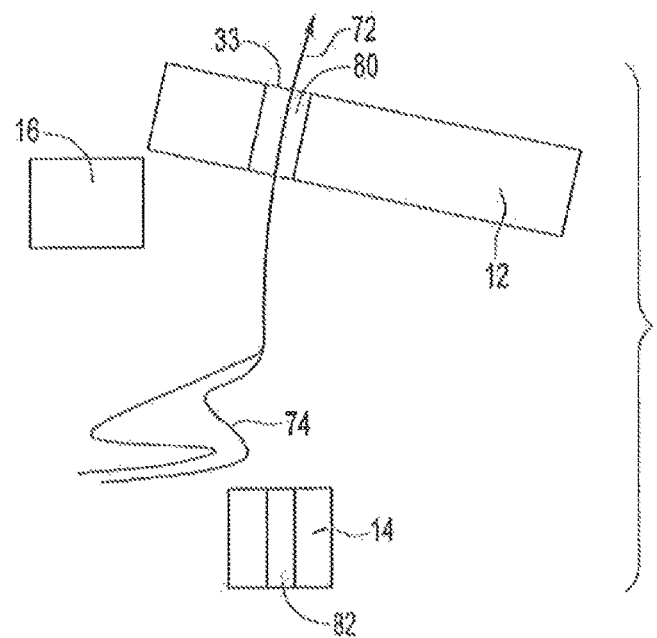
Figure 16C:
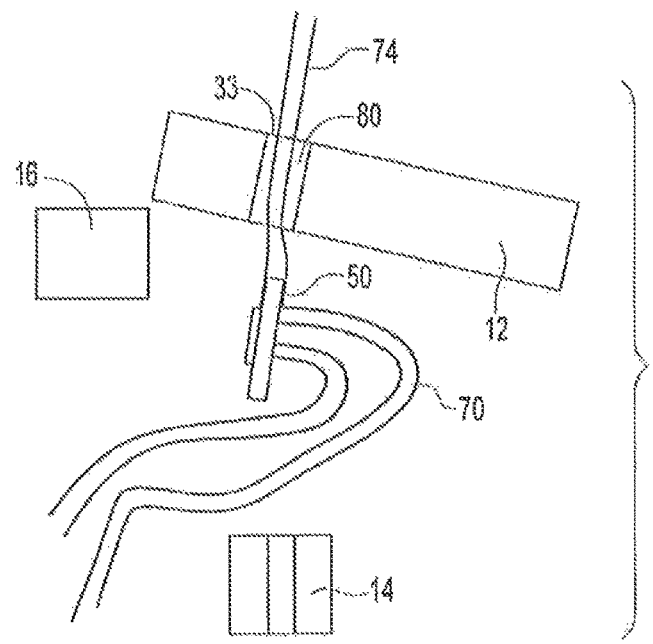

As illustrated in FIG. 16*b*, the long straight needle 72 with pull-through, second suture 74 is passed upwards through the 3.5 mm drill hole 80 in the clavicle 12 and can be passed through the intact skin on the superior aspect of the clavicle 12 or through the open surgical wound. In FIG. 16 *c*, the pull-through suture 74, which engages the first aperture 52 (not shown) of the button 50, can now advance the button 50, substantially longitudinally through the drill hole 80. Engagement of the second suture 74 in the aperture 52 (not shown) ensures that the second suture 74 is located adjacent the longitudinal mid-line of the button 50 so that the second suture 74 stays central in the first aperture 52.

Figure 16D:
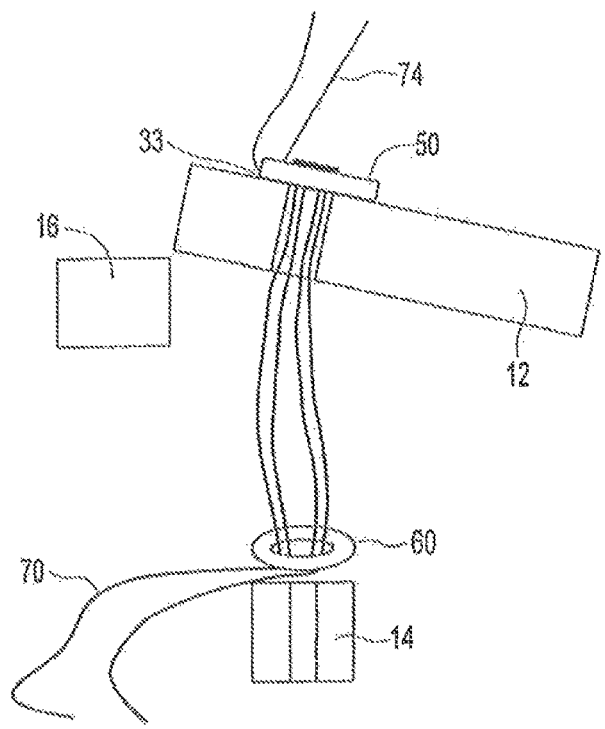
Figure 16E:
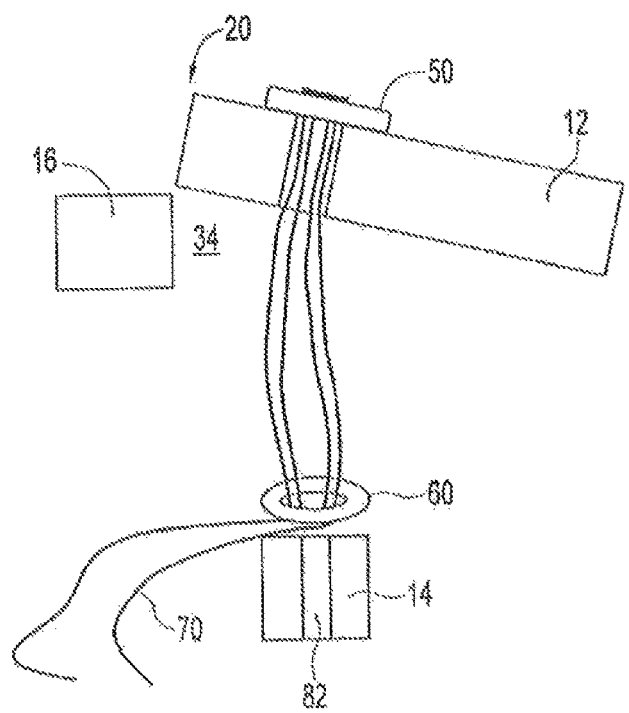
Figure 16F:
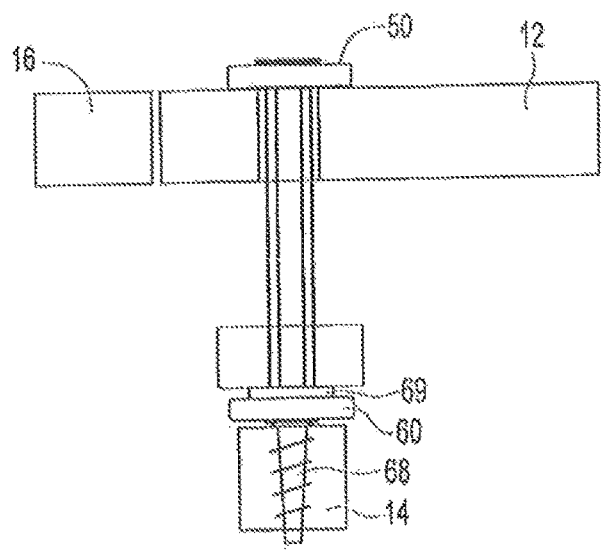

In FIG. 16d, once the button 50 has exited the superior surface 33 of the clavicle 12, the angle of traction on the pull-through, or second, suture 74 is changed and counter-traction is exerted on the first suture 70, in order to flip (pivot) the button 50 and engage the button 50 against the superior surface 33 of the clavicle 12. Once the button 50 is anchored, the pull-through, or second, suture 74 can be cut and removed (FIGS. 16d and 16e). In FIG. 16 f, the screw 68 containing the washer 60 is inserted into the 2.5 mm drill hole 82 (FIG. 16e) in the base of the coracoid process 14 of the scapula. Before the washer 60/bone screw 68 is fully seated into the drill hole 82, the acromioclavicular joint 34 is reduced by downward manual pressure on the lateral end 20 of the clavicle 12 (FIGS. 16e and 16f).

The two trailing ends of the first suture 70 (FIG. 16e) are pulled to approximate the desired distance between the button 50 and the washer 60, and hence reduce the interval between the clavicle 12 and the coracoid process 14. The first suture 70 is then secured to itself with a knot, tied tight by hand. The free ends of the first suture 70 can then be cut approximately 1 cm long, to avoid knot slippage. The screw 68 can then be fully seated into the drill hole 82 in the coracoid process 14 to maximize suture tension, or may be advanced or retracted accordingly to fine tune the suture tension, according to the surgeon's preference.

The volume between the arcuate undersurface 69 of the bone screw 68 and the coracoid process 14 defines the maximum flexibility of the washer 60 therebetween. The designed flexibility is helpful in increasing the tolerance for non-aligned drill holes and the like.

Post-Operative Management

Following wound closure, the shoulder should be placed in a shoulder immobilizer for three weeks. Gentle range of motion exercises can begin after three weeks. Full range exercises can be allowed after six weeks.

Implant Removal

Routine removal of the first suture anchor-suture-second suture anchor construct is not required. If, for any reason, it needs to be removed, this can be performed simply by re-opening the surgical incision, cutting the first suture 70 as it loops through the button 50 and removing the button 50. The screw 68 and washer 60 can be removed easily using the screwdriver.

It is noted that the above description and drawings are exemplary and illustrate preferred embodiments that achieve the objects, features and advantages of the present invention. It is not intended that the present invention be limited to the illustrated embodiments. Any modification of the present invention which comes within the spirit and scope of the following claims should be considered part of the present invention.

What is claimed is:

1. A method of ankle syndesmosis repair, comprising:
   drilling a hole through a fibula and a tibia of an ankle joint using a single drill bit;
   pulling a first button device through the hole using a pull-through suture until the first button device exits on a medial side of the tibia;
   flipping the first button device so it rests against a medial cortex of the tibia; and
   positioning a second button device at a lateral side of the fibula, wherein a flexible suture coupling is connected to the first button device and the second button device.

2. The method as recited in claim 1, comprising reducing a fracture of the fibula prior to drilling the hole.

3. The method as recited in claim 1, wherein pulling the first button device includes:
   connecting the first button device to a suture passing instrument with the pull-through suture; and
   inserting the suture passing instrument through the hole to advance the first button device horizontally through the hole.

4. The method as recited in claim 3, wherein flipping the first button device includes:
   applying traction to the pull-through suture while applying counter-traction to the flexible suture coupling connected to the first button device until the first button device pivots from a position generally parallel to the hole to a position generally transverse to the hole.

5. The method as recited in claim 1, wherein the flexible suture coupling is double looped through the first button device and the second button device.

6. The method as recited in claim 1, wherein positioning the second button device includes:
   tightening down the second button device on the lateral side of the fibula by applying traction to a free end of the flexible suture coupling connected to each of the first button device and the second button device.

7. The method as recited in claim 1, wherein the first button device and the second button device each include at least one aperture.

8. The method as recited in claim 1, wherein pulling the first button device includes:
   passing an elongated pull-through device that is connected to the pull-through suture through the hole.

9. The method as recited in claim 1, comprising reducing a syndesmosis disruption prior to performing the drilling, pulling, flipping and positioning steps.

10. A method of ankle syndesmosis repair, comprising:
    reducing a syndesmosis disruption of an ankle joint;
    drilling a hole through a fibula and a tibia of the ankle joint using a single drill bit;
    pulling, in a lateral-to-medial direction of the ankle joint, a first button device through the hole with a pull-through suture until the first button device exits on a medial side of the tibia;
    flipping the first button device so it rests against a medial cortex of the tibia;
    positioning a second button device at a lateral side of the fibula, wherein a flexible suture coupling is connected to the first button device and the second button device; and
    tightening down the second button device on the lateral side of the fibula by applying traction to a free end of the flexible suture coupling.

* * * * *